United States Patent
Ogura

(10) Patent No.: US 9,552,959 B2
(45) Date of Patent: Jan. 24, 2017

(54) SAMPLE HOLDER FOR SCANNING ELECTRON MICROSCOPE, SCANNING ELECTRON MICROSCOPE IMAGE OBSERVATION SYSTEM, AND SCANNING ELECTRON MICROSCOPE IMAGE OBSERVATION METHOD

(71) Applicant: NATIONAL INSTITUTE OF ADVANCED INDUSTRIAL SCIENCE AND TECHNOLOGY, Chiyoda-ku (JP)

(72) Inventor: Toshihiko Ogura, Ibaraki (JP)

(73) Assignee: NATIONAL INSTITUTE OF ADVANCED INDUSTRIAL SCIENCE AND TECHNOLOGY, Chiyoda-ku (JP)

( * ) Notice: Subject to any disclaimer, the term of this patent is extended or adjusted under 35 U.S.C. 154(b) by 0 days.

(21) Appl. No.: 14/783,310

(22) PCT Filed: Mar. 24, 2014

(86) PCT No.: PCT/JP2014/001668
§ 371 (c)(1),
(2) Date: Oct. 8, 2015

(87) PCT Pub. No.: WO2014/167787
PCT Pub. Date: Oct. 16, 2014

(65) Prior Publication Data
US 2016/0056012 A1    Feb. 25, 2016

(30) Foreign Application Priority Data

Apr. 8, 2013    (JP) ................. 2013-080490

(51) Int. Cl.
*H01J 37/20* (2006.01)
*H01J 37/244* (2006.01)
(Continued)

(52) U.S. Cl.
CPC ............ *H01J 37/20* (2013.01); *H01J 37/22* (2013.01); *H01J 37/244* (2013.01); *H01J 37/28* (2013.01);
(Continued)

(58) Field of Classification Search
USPC .................................... 250/440.11
See application file for complete search history.

(56) References Cited

U.S. PATENT DOCUMENTS 7,239,148 B2 * 7/2007 Suhara ............ G03F 7/70675
324/452
8,232,522 B2 * 7/2012 Miya ................. H01J 37/265
250/306
(Continued)

FOREIGN PATENT DOCUMENTS

JP    2004-515049 A    5/2004
JP    2008-210715 A    9/2008
(Continued)

OTHER PUBLICATIONS

Toshihiko Ogura "A high contrast method of unstained biological samples under a thin carbon film by scanning electron microscopy" Biochemical and Biophysical Research Communications, vol. 377, pp. 79-84 (2008).
(Continued)

*Primary Examiner* — Phillip A Johnston
(74) *Attorney, Agent, or Firm* — Oblon, McClelland, Maier & Neustadt, L.L.P.

(57) ABSTRACT

A water solution in which an observation sample is, for example, dissolved is sandwiched on a first insulative thin film side provided under a conductive thin film. When an electron beam incident part is charged minus, electric dipoles of water molecules are arrayed along a potential gradient. Electric charges are also generated on the surface
(Continued)

of a second insulative thin film. The electric charges are detected by a terminal section and changes to a measurement signal. In a state in which an electron beam is blocked, the minus potential disappears. Consequently, the electric charges on the surface of the first insulative thin film also disappear, and the measurement signal output from the terminal section changes to 0.

10 Claims, 10 Drawing Sheets

(51) Int. Cl.
*H01J 37/28* (2006.01)
*H01J 37/22* (2006.01)

(52) U.S. Cl.
CPC ... *G01N 2223/309* (2013.01); *G01N 2223/418* (2013.01); *H01J 2237/153* (2013.01); *H01J 2237/2003* (2013.01); *H01J 2237/2007* (2013.01); *H01J 2237/2608* (2013.01); *H01J 2237/2801* (2013.01)

(56) References Cited

U.S. PATENT DOCUMENTS

| | | |
|---|---|---|
| 2004/0046120 A1 | 3/2004 | Moses et al. |
| 2008/0308731 A1 | 12/2008 | Nishiyama et al. |
| 2009/0103236 A1* | 4/2009 | Nonaka ............... C03C 17/007 361/320 |
| 2012/0321037 A1 | 12/2012 | Ogura |
| 2014/0346352 A1 | 11/2014 | Ogura |
| 2015/0214003 A1 | 7/2015 | Ogura |

FOREIGN PATENT DOCUMENTS

| | | |
|---|---|---|
| JP | 2008-210765 A | 9/2008 |
| JP | 2010-097844 A | 4/2010 |
| JP | 2010-175389 A | 8/2010 |
| JP | 2011-007766 A | 1/2011 |
| JP | 5115997 B1 | 1/2013 |
| JP | 2014-22323 A | 2/2014 |
| WO | 02/45125 A1 | 6/2002 |

OTHER PUBLICATIONS

Toshihiko Ogura "Direct observation of the inner structure of unstained atmospheric cells by low-energy electrons" Measurement Science and Technology, http://iopscience.iop.org/0957-0233/23/8/085402, vol. 23, pp. 1-8, (2012).
Stephan Thiberge, et al., "Scanning electron microscopy of cells and tissues under fully hydrated conditions" Proceedings of the National Academy of Sciences, vol. 101, No. 10, pp. 3346-3351, (Mar. 9, 2004).
International Search Report issued on Apr. 22, 2014 for PCT/JP2014/001668 filed on Mar. 24, 2014.
Extended European Search Report issued Nov. 4, 2016, in Europe Patent Application No. 14783084.8/1556/2985780 PCT/JP2014001668.

* cited by examiner

FIG.7
(a)
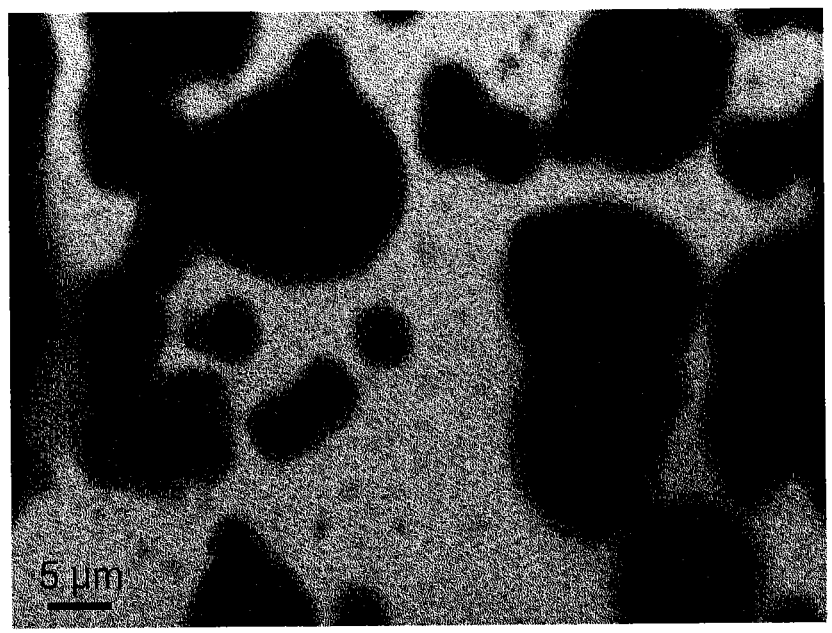
(b)
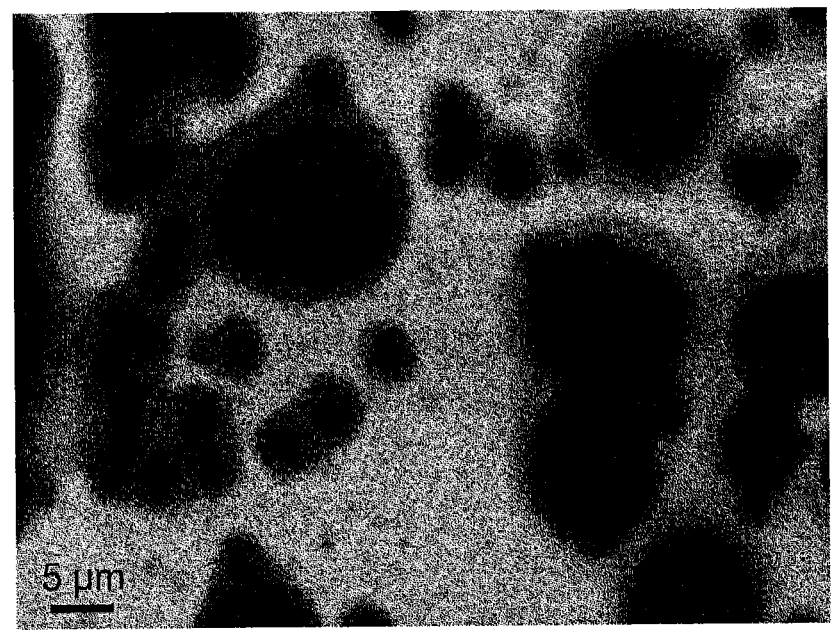

FIG.9
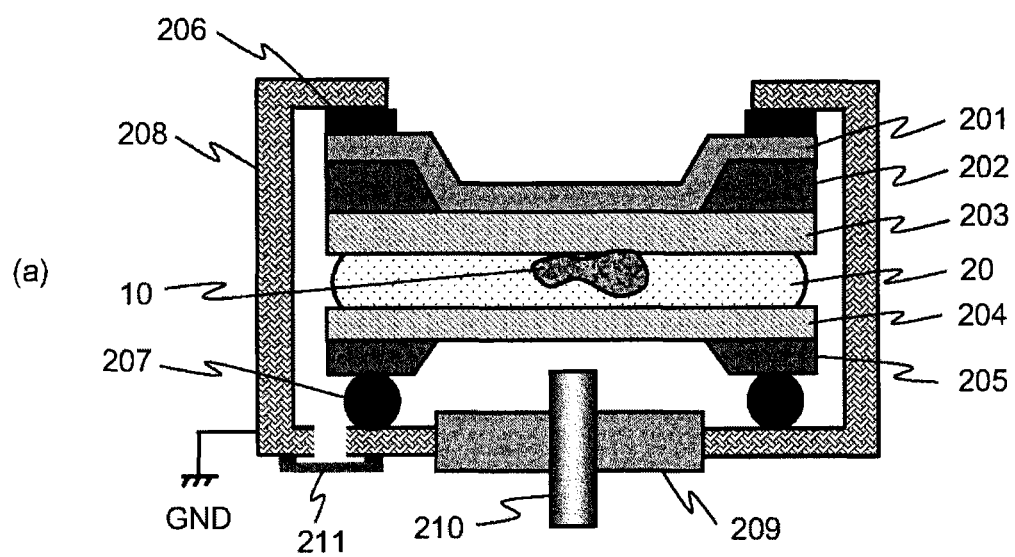
(a)
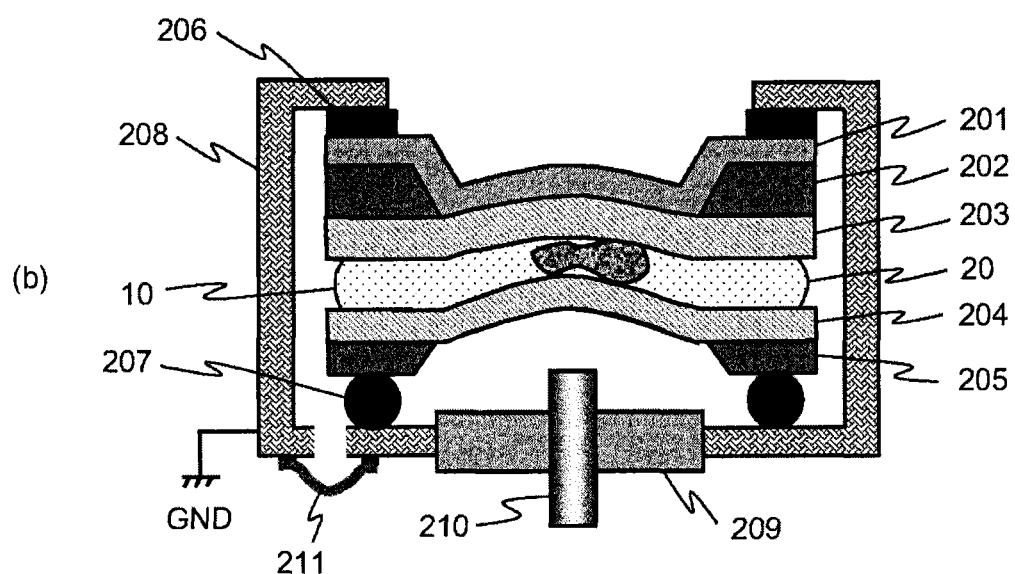
(b)

FIG.10
(a)
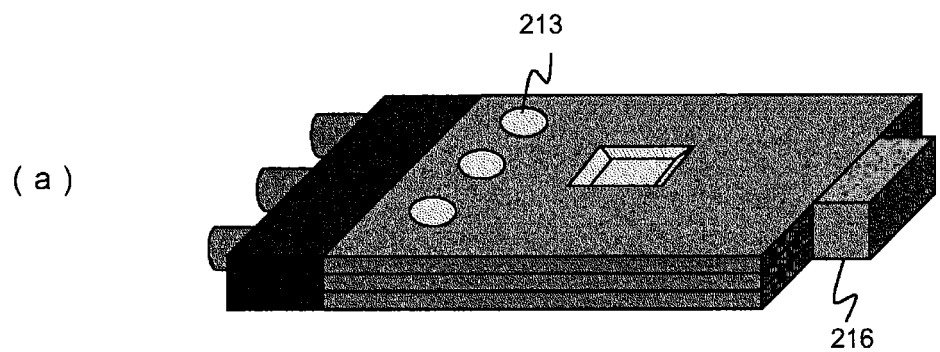
(b)
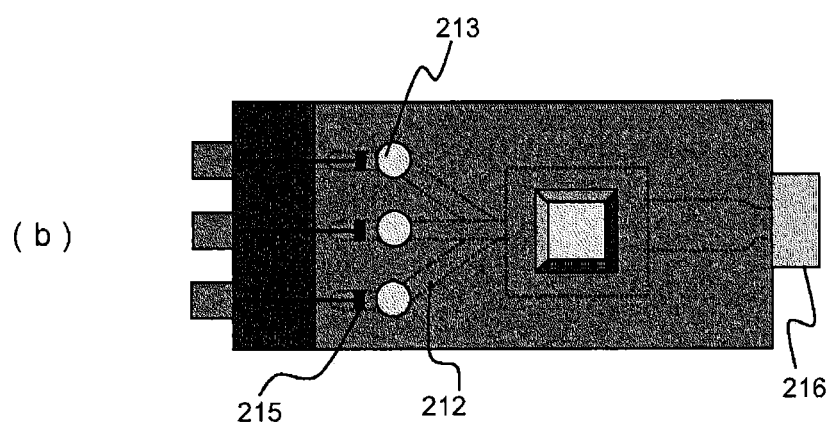
(c)
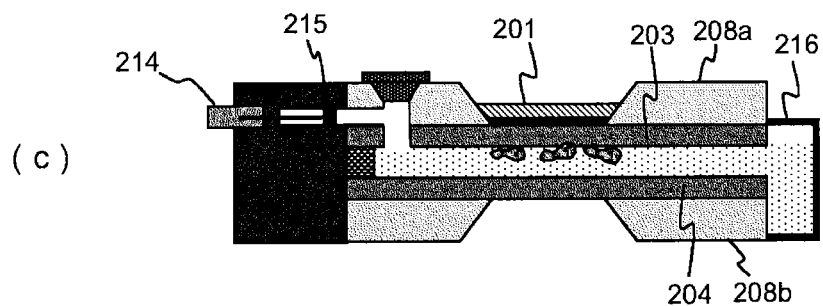

SAMPLE HOLDER FOR SCANNING ELECTRON MICROSCOPE, SCANNING ELECTRON MICROSCOPE IMAGE OBSERVATION SYSTEM, AND SCANNING ELECTRON MICROSCOPE IMAGE OBSERVATION METHOD

TECHNICAL FIELD

The present invention relates to an observation technique by a scanning electron microscope. More specifically, the present invention relates to a scanning electron microscope observation technique also capable of observing a biological sample in a living state.

BACKGROUND ART

A scanning electron microscope is widely used as a tool in observing a biological sample and an organic sample at high resolution. Conventionally, when the biological sample and the organic sample are observed by the scanning electron microscope, in order to reduce electron beam damage to an observation target sample and obtain an image with high contrast, it has been considered essential to perform treatment for, for example, after fixing the sample with formaldehyde or the like, coating the surface of the sample with gold, platinum, carbon, or the like or applying dying by heavy metal to the sample.

However, in recent years, a method with which a biological sample can be observed at high contrast without coating and dying has been developed (see Patent Literature 1 and Non Patent Literature 1).

In this new method, a sample is deposited on a lower surface of a thin sample supporting film such as a carbon film and an electron beam with a low acceleration voltage is irradiated on the sample from above the sample supporting film. The irradiated electron beam spreads while diffusing on the inside of the sample supporting film and reaches near the lower surface of the film. Secondary electrons are emitted from the lower surface of the sample supporting film. The secondary electrons are absorbed by the sample immediately below the sample supporting film. Consequently, it is possible to obtain an image with extremely high contrast.

In this method, a condition is set such that energy of the secondary electrons is approximately 10 eV. With such extremely weak secondary electrons, electron beam damage to the observation target sample is markedly low. Therefore, even in a sample susceptible to damage such as a biological sample, an original shape and an original structure of the sample can be observed or analyzed with an image with high contrast. Such an observation condition is called "indirect secondary electron contrast condition".

Such an observation method is further promoted to also develop a method of forming a conductive film below an insulative thin film layer and further improve resolution and contrast by making use of a charging effect by electron beam incidence (see Patent Literature 2 and Non Patent Literature 2).

CITATION LIST

Patent Literature

Patent Literature 1: Japanese Patent Laid-Open No. 2010-097844
Patent Literature 2: Japanese Patent No. 5115997

Non Patent Literature

Non Patent Literature 1: T. Ogura "A high contrast method of unstained biological samples under a thin carbon film by scanning electron microscopy" Biochem. Biophys. Res. Commun. Vol. 377, p 79-84 (2008)
Non Patent Literature 2: T. Ogura "Direct observation of the inner structure of unstained atmospheric cells by low-energy electrons" Meas. Sci. Technol. Vol. 23, 085402(8 pp) (2012)
Non Patent Literature 3: S. Thiberge et al. "Scanning electron microscopy of cells and tissues under fully hydrated conditions" PNAS. Vol. 101, p 3346-3351 (2004)

SUMMARY OF INVENTION

Technical Problem

Currently, an exclusive holder for enabling observation of a biological sample in a water solution (see Non Patent Literature 3) and an electron microscope system capable of performing biological sample observation under the atmospheric pressure have also been developed. However, damage to the biological sample by an electron beam is serious even in these methods. Moreover, since interaction between the electron beam and the biological sample is extremely weak, it is extremely difficult to observe the biological sample in the water solution in a living state at high contrast.

From such circumstances, in order to clearly observe the biological sample, it is necessary to apply dying treatment and fixation treatment, reduce the damage by the electron beam, and improve contrast of an observation image (Non Patent Literature 3).

However, when such treatment is applied, the biological sample, which is an observation target, dies out and the observation in the living state cannot be performed. Moreover, various artifacts involved in the dying treatment and the like occur. Reliability of an image obtained by the observation is damaged. In addition, such dying treatment and the like not only require expert skills but also are undesirable from the viewpoint of environmental protection because a toxic substance such as uranium acetate is used as a dying agent.

An image observed under the "indirect secondary electron contrast condition" has an advantage that contrast is extremely high and, on the other hand, has a problem in that resolution is relatively low. Further, usually, it is difficult to cause secondary electrons with low energy to penetrate into a water solution having thickness (depth) of several micrometers or more. Therefore, it is difficult to observe a biological sample present in the water solution.

In this way, in the conventional observation technique, it is extremely difficult to observe a biological sample in a water solution in a living state and obtain an image with high resolution on which an original form and an original structure of the biological sample are correctly reflected.

The present invention has been devised in view of such problems and it is an object of the present invention to provide a scanning electron microscope observation technique for making it possible to observe a biological sample in a living state at high resolution and high contrast using a scanning electron microscope without applying dying treatment and fixation treatment.

Solution to Problem

In order to solve such a problem, a sample holder for a scanning electron microscope according to the present invention includes a first insulative thin film, one principal plane of which is a holding surface for an observation sample, and a conductive thin film stacked on the other principal plane of the first insulative thin film. On the one principal plane side of the first insulative thin film, a terminal section that detects a signal based on the potential of the one principal plane of the first insulative thin film caused by an electron beam made incident from the conductive thin film side is provided.

For example, a second insulative thin film is provided between the one principal plane of the first insulative thin film and the terminal section. One principal plane of the second insulative thin film and the one principal plane of the first insulative thin film are disposed to have a gap of a predetermined interval. The terminal section detects the potential of the other principal plane of the second insulative thin film as a signal.

Preferably, the thickness of the first insulative thin film is 200 nm or less.

For example, the first insulative thin film is made of a silicon nitride film, a carbon film, or a polyimide film.

Preferably, the thickness of the conductive thin film is 100 nm or less.

Preferably, the conductive thin film is a metal thin film containing, as a main component, metal having a specific gravity of 10 g/cm$^3$ or more.

For example, the metal thin film contains any one of tantalum, tungsten, rhenium, molybdenum, osmium, gold, and platinum as a main component.

Preferably, the interval between the one principal plane of the first insulative thin film and the one principal plane of the second insulative thin film can be set to 40 µm or less.

Preferably, the sample holder for the scanning electron microscope includes an outer frame section that seals the inside of the sample holder, and an adjusting mechanism for internal pressure is provided in the outer frame section.

Further, preferably, in the sample holder for the scanning electron microscope, a channel for perfusing the water solution is provided in the gap of the predetermined interval between the one principal plane of the second insulative thin film and the one principal plane of the first insulative thin film.

A scanning electron microscope image observation system according to the present invention includes: a scanning electron microscope; the sample holder for the scanning electron microscope set in the scanning electron microscope; and an arithmetic unit that processes, as an output signal detected by the terminal section, a signal based on potential of the one principal plane of the first insulative thin film or a potential signal of the other principal plane of the second insulative thin film.

Preferably, the arithmetic unit processes the output signal, extracts a signal component having an intensity change frequency from the output signal, and forms an image on the basis of the extracted signal frequency having the intensity change frequency.

For example, the extraction of the signal component having the intensity change frequency is performed by any one of a band pass filter method, a lock-in amplifier method, an autocorrelation analysis method, and a Fourier transform analysis method.

Preferably, a plurality of the terminal sections are provided in different positions, and the arithmetic unit forms an image for each of signal components having the intensity change frequency respectively extracted from the plurality of terminal sections, calculates an inclination angle of the image from a relation between an incident position of an electron beam and the positions where the terminal sections are provided, applies correction to the image on the basis of the inclination angle, and analyzes three-dimensional structure information of an observation sample on the basis of a plurality of images after the correction.

A scanning electron microscope image observation method according to the present invention performs, using the scanning electron microscope image observation system, observation in a state in which the conductive thin film is set to a ground potential of the scanning electron microscope or a predetermined potential.

A scanning electron microscope image observation method according to the present invention performs, using the scanning electron microscope image observation system, observation with an acceleration voltage of the incident electron beam set to a voltage at which the incident electron beam is hardly transmitted through the first insulative thin film.

A scanning electron microscope image observation method according to the present invention performs, using the scanning electron microscope image observation system, observation with an acceleration voltage of the incident electron beam set to 10 kV or less.

A scanning electron microscope image observation method according to the present invention turns on and off, using the scanning electron microscope image observation system, the incident electron beam at a frequency of 1 kHz or more and performs observation with the extracted intensity change frequency set to 1 kHz or more.

Further, a scanning electron microscope image observation method according to the present invention performs, using the scanning electron microscope image observation system, observation in a state in which an observation sample is supported on the one principal plane of the first insulative thin film together with a water solution.

Advantageous Effects of Invention

According to the present invention, it is possible to easily observe a biological sample in a water solution at extremely high contrast without applying dying treatment and fixation treatment to the biological sample. In addition, since damage to the sample due to an electron beam does not occur, it is possible to learn original forms and structures concerning biological samples such as cells, bacteria, viruses, and protein complexes and organic materials susceptible to damage.

BRIEF DESCRIPTION OF DRAWINGS

FIG. 4 is a diagram for conceptually explaining a mechanism in which a signal is detected in a terminal section when an electron beam, intensity of which changes in a rectangular wave shape, is made incident on the sample holder according to the present invention, wherein FIG. 4(a) shows a state in which the electron beam is made incident (an ON state) and FIG. 4(b) shows a state in which the electron beam is blocked by a diaphragm and is not made incident (an OFF state).

FIG. 7 is an observation image obtained by storing yeast dissolved in the water solution in the sample holder for the scanning electron microscope according to the present invention and observing the yeast, wherein FIG. 7(a) is an observation image in the case in which an ON/OFF frequency of an incident electron beam is 30 kHz and FIG. 7(b) is an observation image in the case in which the ON/OFF frequency of the incident electron beam is 80 kHz.

FIG. 9 is a diagram for explaining the structure of the sample holder having a form in which a mechanism for adjusting the pressure on the inside of an outer frame section is provided.

FIG. 10 is a configuration example of the sample holder in which channels for perfusing the water solution is provided in a gap of a predetermined interval between one principal plane of a second insulative thin film and one principal plane of a first insulative thin film, wherein FIGS. 10(a) to 10(c) are respectively a perspective view, a top view, and a sectional view.

DESCRIPTION OF EMBODIMENTS

Modes for carrying out the present invention are explained below with reference to the drawings.

Figure 1:
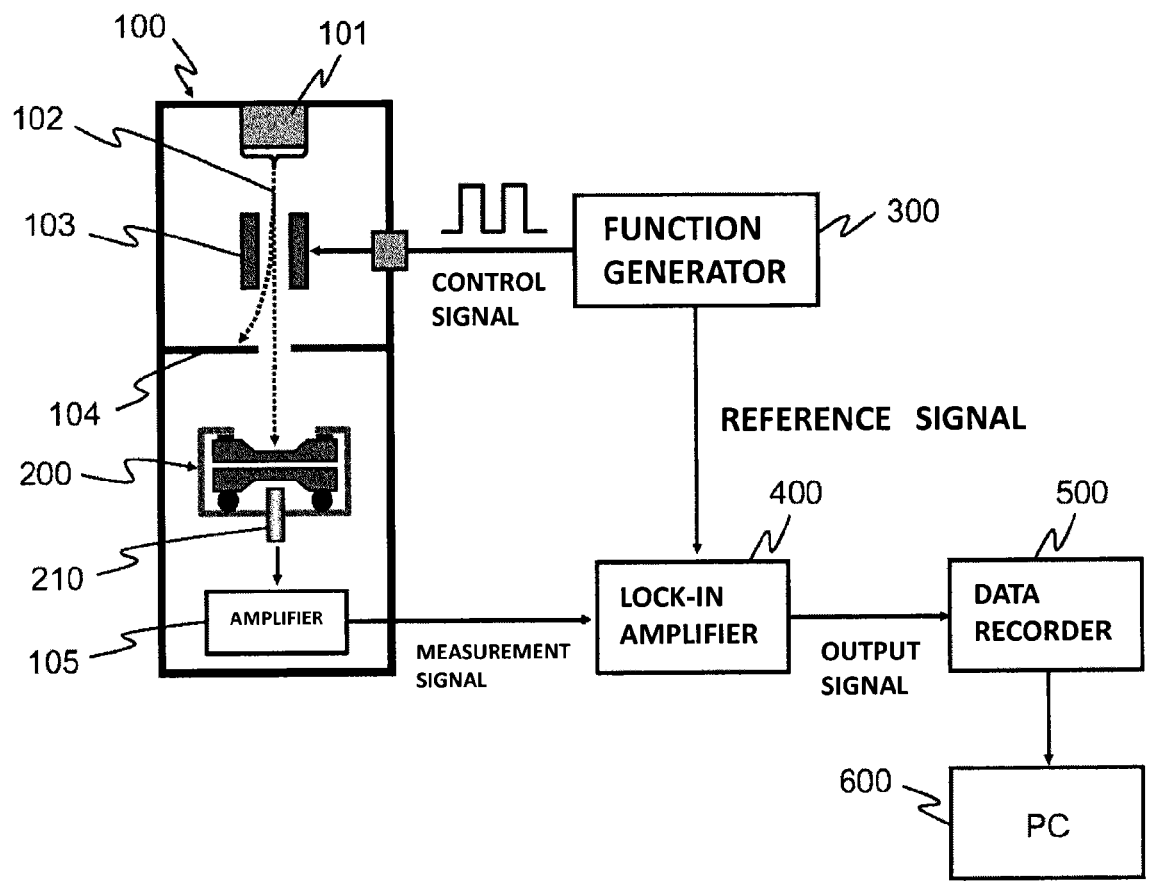
FIG. 1 is a block diagram for explaining a configuration example of a scanning electron microscope image observation system according to the present invention.

FIG. 1 is a block diagram for explaining a configuration example of a scanning electron microscope image observation system according to the present invention.

In an example shown in the figure, the system includes a scanning electron microscope 100, a sample holder 200 for a scanning electron microscope set on the inside of the scanning electron microscope 100, a function generator 300, a lock-in amplifier 400, a data recorder 500, and a PC 600 functioning as an arithmetic unit.

In the scanning electron microscope 100, a beam blanking device 103 for controlling irradiation intensity on an observation sample of an electron beam 102 emitted from an electron gun 101 is provided. The beam blanking device 103 is a device for obtaining an intensity change of an incident electron beam on the observation sample. For example, an ON/OFF signal having a frequency of 1 kHz or more is input to the beam blanking device 103 as a control signal having a rectangular wave form from the function generator 300 provided outside a microscope chamber. The function generator 300 outputs a reference signal to the lock-in amplifier 400.

When a control signal for OFF is input from the function generator 300, the electron beam 102 emitted from the electron gun 101 travels forward. The entire electron beam 102 is transmitted through a diaphragm 104 and irradiated on an observation sample (not shown in the figure) stored in the sample holder 200.

On the other hand, when a control signal for ON is input from the function generator 300, an electric field is generated in the vicinity of the beam blanking device 103 and a track of the electron beam 102 emitted from the electron gun 101 is bent. The entire (or a part of) electron beam 102 is blocked by the diaphragm 104.

As a result, when the control signal has plus potential, an electric field is generated in the beam blanking device 103. An electron beam is bent by a Coulomb force and blocked by the diaphragm 104. The electron beam made incident on the observation sample is turned off. On the other hand, when the control signal has zero potential, the electron beam is transmitted through the diaphragm 104 and irradiated on the observation sample.

When ON/OFF by such a control signal is repeated, the intensity of the electron beam irradiated on the observation sample changes. The frequency of the control signal at this point is suitably 1 kHz or more. In general, the frequency is set in a range of 20 to 100 kHz.

That is, according to the control signal input from the function generator 300, the intensity of the electron beam irradiated on the observation sample (not shown in the figure) stored in the sample holder 200 changes at a frequency same as the frequency of the control signal.

When the electron beam is irradiated on the observation sample stored in the sample holder 200, because of a reason explained below, a signal based on potential caused by the incidence of the electron beam is generated in the sample holder 200. The signal is detected by a terminal section 210 provided under the sample holder 200, amplified by an amplifier 105, and output to the lock-in amplifier 400 as a measurement signal. That is, the reference signal from the function generator 300 and the measurement signal from the amplifier 105 are input to the lock-in amplifier 400.

The lock-in amplifier 400 extracts only a frequency component of the reference signal of the function generator 300 out of the measurement signal using the reference signal and transmits the frequency component to the data recorder 500 as an output signal.

The PC 600 functioning as the arithmetic unit processes the output signal, extracts a signal component having an intensity change frequency from the output signal, and forms an image on the basis of the extracted signal component having the intensity change frequency according to the scanning signal of the electron beam. The extraction of the signal component having the intensity change frequency can be performed by a method such as a band pass filter method, a lock-in amplifier method, an autocorrelation analysis method, or a Fourier transform analysis method.

Figure 2:
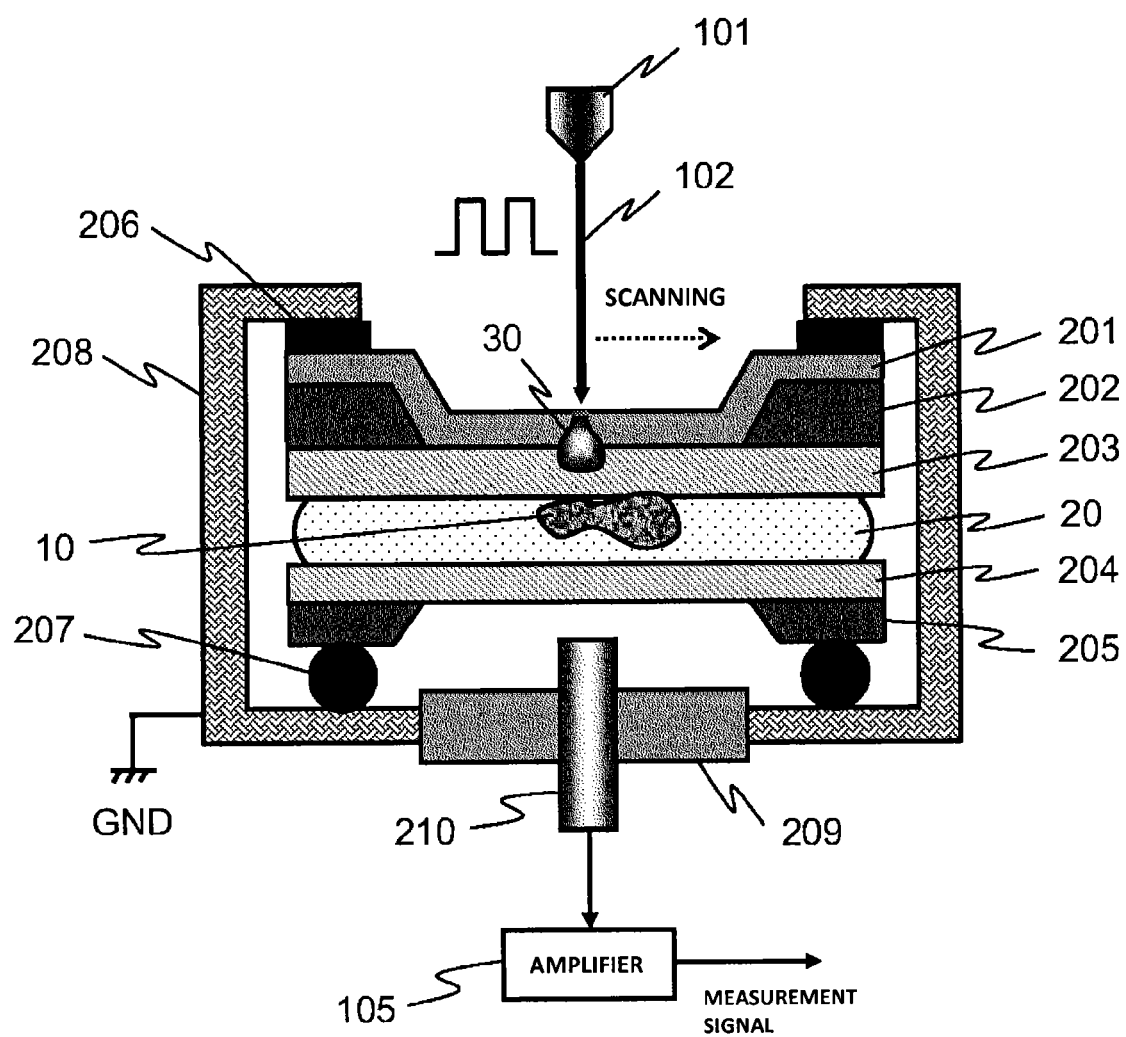
FIG. 2 is a schematic sectional view for explaining a configuration example of a sample holder for the scanning electron microscope according to the present invention.

FIG. 2 is a schematic sectional view for explaining a configuration example of a sample holder for the scanning electron microscope according to the present invention.

The sample holder 200 includes a first insulative thin film 203, one principal plane of which is a holding surface for an observation sample 10, and a conductive thin film 201 stacked on the other principal plane of the first insulative thin film 203. The stacked body has pressure resistance enough for withstanding observation in a vacuum. That is, in an electron microscope chamber, an atmospheric pressure state can be retained in the holder. On the one principal plane side of the first insulative thin film 203, the terminal section 210 that detects a signal based on the potential of the one principal plane of the first insulative thin film 203 caused by the electron beam 102 made incident from the conductive thin film 201 side is provided.

In the configuration example shown in the figure, a second insulative thin film 204 is provided between the one principal plane of the first insulative thin film 203 and the terminal section 210. One principal plane of the second insulative thin film 204 and the one principal plane of the first insulative thin film 203 are disposed to have a gap of a predetermined interval. Therefore, in the case of this configuration, the terminal section 210 detects the potential of the other principal plane of the second insulative thin film 204 as a signal. In a state in which the terminal section 210 is electrically insulated from the first insulative thin film 203 and the second insulative thin film 204 functioning as sample supporting films, the terminal section 210 is provided to be separated from these thin films.

Note that the second insulative thin film 204 is not essential. For example, if an observation sample can be, for example, dissolved in an extremely thin layer of water, the observation sample is held by the surface tension of the water layer. Therefore, even if the second insulative thin film 204 is absent, a signal based on the potential of the one principal plane of the first insulative thin film 203 can be detected by the terminal section 210.

The observation sample 10 may be a biological sample present in a water solution 20. The observation sample 10 is encapsulated between the first insulative thin film 203 and the second insulative thin film 204 and stored in a conductive outer frame section 208, the inside of which is sealed by a conductive gasket 206 and an O-ring 207. That is, observation in a state in which the biological sample is supported together with the water solution is possible.

Note that, as explained below, a mechanism for adjusting the pressure on the inside may be provided in the outer frame section 208. A member denoted by reference numeral 209 is an insulating member for insulating the terminal section 210 from the outer frame section 208. Sections denoted by reference numerals 202 and 205 are frame sections provided for the purpose of strength maintenance. Reference numeral 30 denotes a diffusion region of the incident electron beam 102.

In the example shown in FIG. 2, both of the gasket 206 and the outer frame section 208 are conductive. The conductive thin film 201 is set to a ground potential of the scanning electron microscope 100. Observation is performed in this state. Note that the observation may be performed in a state in which the potential of the conductive thin film 201 is set to a predetermined potential rather than the ground potential.

An acceleration voltage of the electron beam 102 emitted from the electron gun 101 is desirably set to a voltage at which an incident electron beam is hardly transmitted through the first insulative thin film 203. Specifically, the acceleration voltage is desirably set to an acceleration voltage at which the incident electron beam is almost scattered or absorbed on the inside of the conductive thin film 201. According to such voltage setting, primary electrons are hardly transmitted to the first insulative thin film 203 side. It is possible to completely prevent electron beam damage to the observation sample 10.

In general, if the acceleration voltage of the incident electron beam is set to 10 kV or less, the condition is realized.

If the first insulative thin film 203 is too thick, the intensity of a signal detected by the terminal section 210 decreases. Therefore, the thickness of the first insulative thin film 203 is desirably set to 200 nm or less.

As the material of the first insulative thin film 203, a silicon nitride film, a carbon film, and a polyimide film can be illustrated.

If the conductive thin film 201 is too thick, the intensity of the signal detected by the terminal section 210 also decreases. Therefore, the thickness of the conductive thin film 201 is desirably set to 100 nm or less.

The conductive thin film 201 is desirably a metal thin film containing, as a main component, metal having a specific gravity of 10 $g/cm^3$ or more. This is for the purpose of efficiently suppressing blocking properties of the electron beams and internal diffusion of incident electrons. As such a metal thin film, a metal thin film containing any one of tantalum, tungsten, rhenium, molybdenum, osmium, gold, and platinum as a main component can be illustrated.

Figure 3:
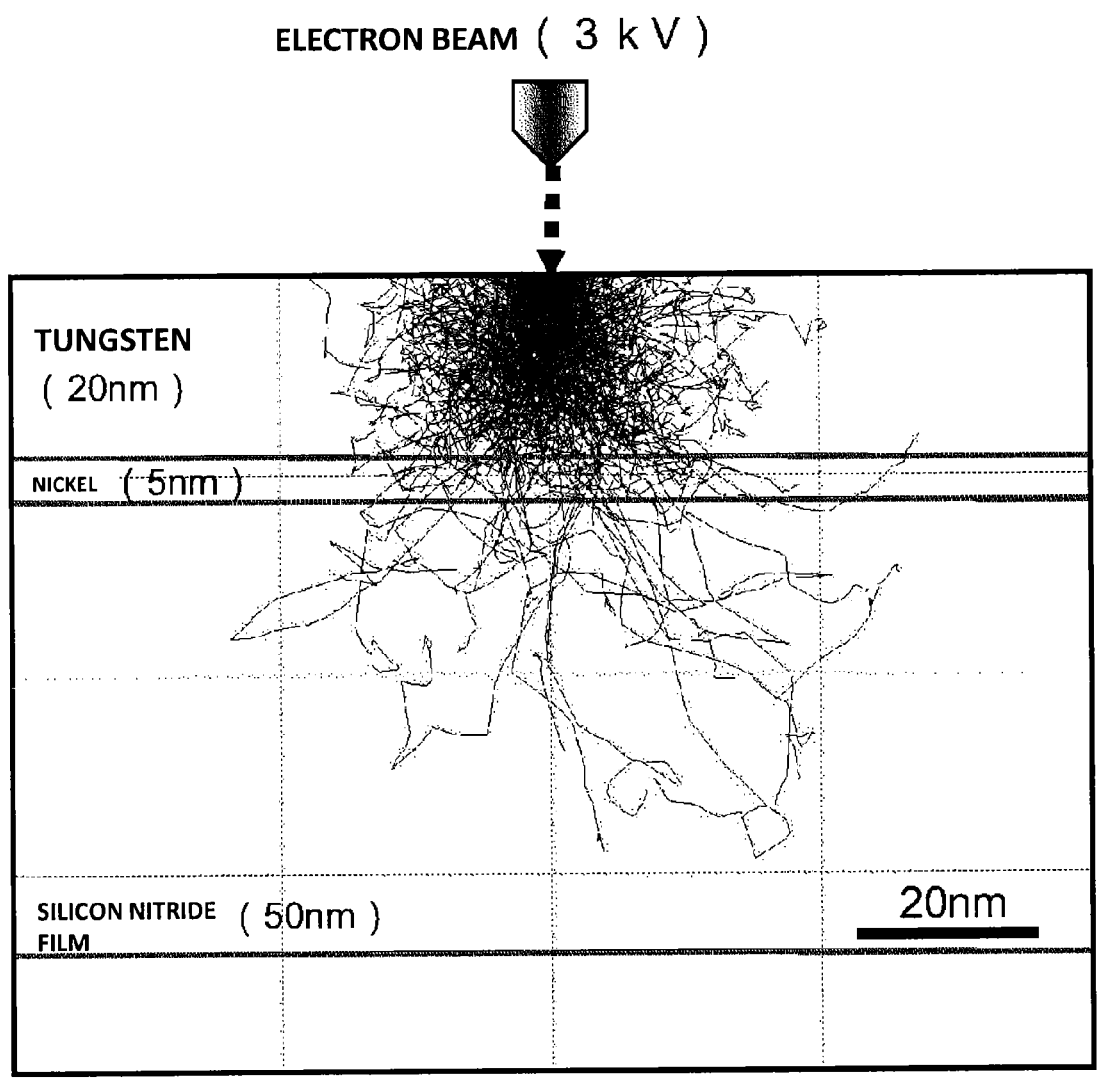
FIG. 3 is a result obtained by stacking nickel having thickness of 5 nm and tungsten having thickness of 20 nm on a silicon nitride thin film having thickness of 50 nm and calculating, with a Monte Carlo simulation, a scattering state at the time when an electron beam is made incident on a stacked film of nickel/tungsten.

FIG. 3 is a result obtained by stacking nickel having thickness of 5 nm and tungsten having thickness of 20 nm on a silicon nitride thin film having thickness of 50 nm and calculating, with a Monte Carlo simulation, a scattering state at the time when an electron beam having an acceleration voltage of 3 kV is made incident on a stacked film of nickel/tungsten.

Most of incident electrons are scattered or absorbed in a tungsten film having a specific gravity of 19.3 $g/cm^3$. Only a part of the electrons scatter to the silicon nitride thin film. However, all of the electrons are absorbed in the silicon nitride thin film. That is, the primary electrons are hardly transmitted through the silicon nitride thin film, which is the first insulative thin film.

When the interval between the one principal plane of the first insulative thin film 203 and the one principal plane of the second insulative thin film 204 is too thick, the intensity of the signal detected by the terminal section 210 decreases. Therefore, the interval can be desirably set to 40 μm or less.

The observation sample 10 is stored in the sample holder 200. The electron beam 102 is made incident while being turned on and off at a frequency of 1 kHz or more. Observation is performed with an intensity change frequency extracted by the lock-in amplifier 400 set to the frequency (1 kHz or more) of the electron beam 102.

Figure 4:
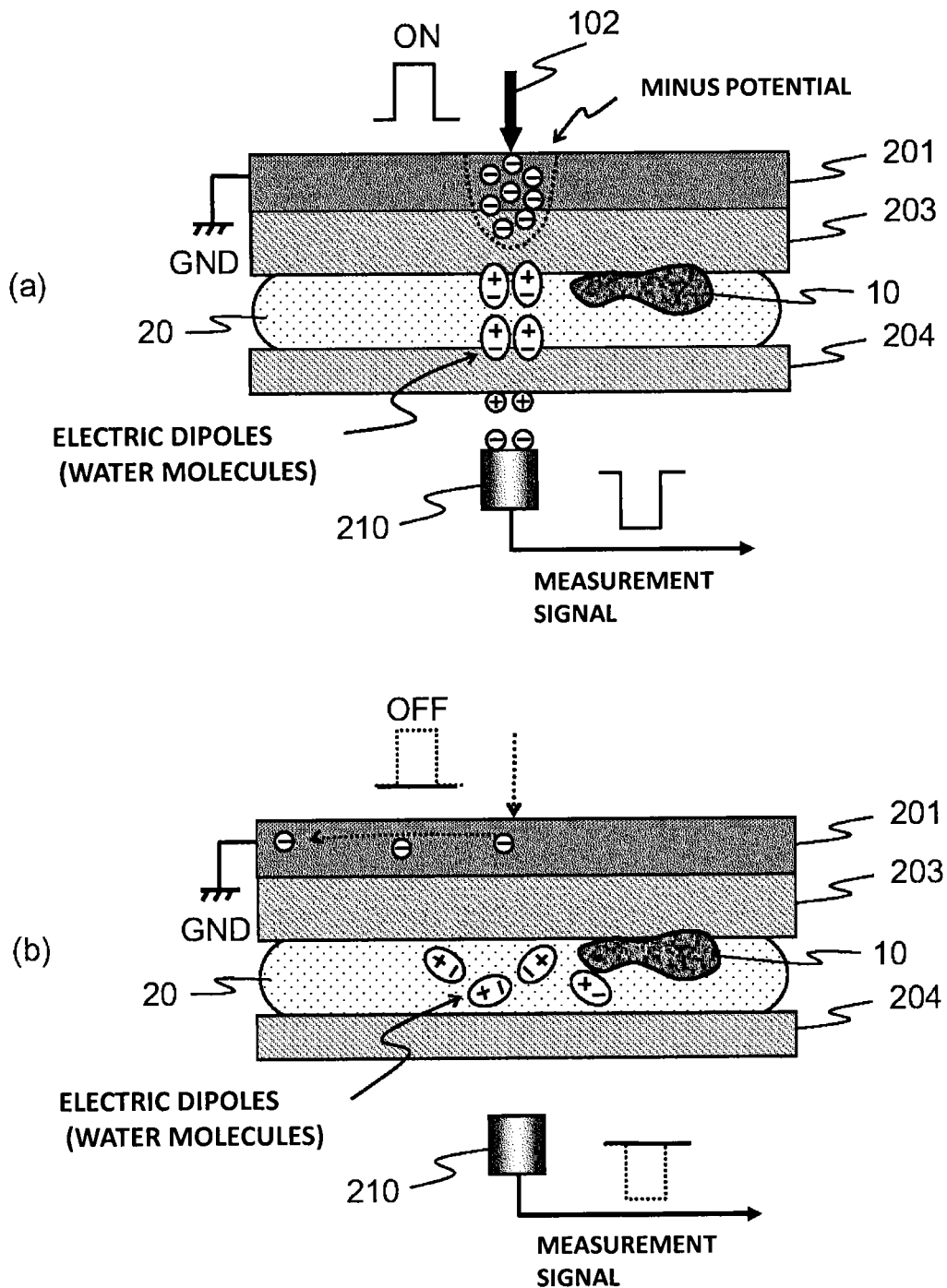

FIG. 4 is a diagram for conceptually explaining a mechanism in which a signal is detected by the terminal section 210 when the electron beam 102, intensity of which changes in a rectangular wave shape, is made incident on the sample holder 200 according to the present invention. FIG. 4(a) shows a state in which the electron beam is made incident (an ON state) and FIG. 4(b) shows a state in which the electron beam is blocked by a diaphragm and is not made incident (an OFF state).

As shown in FIG. 4(a), in the state in which the electron beam 102 is made incident (the ON state), almost all incident electrons are scattered or absorbed in the conductive thin film 201. Consequently, electrons are accumulated in an incident part of the electron beam. The part changes to minus potential.

The water solution 20 in which the observation sample 10 is, for example, dissolved is sandwiched between the first insulative thin film 203 and the second insulative thin film 204. Since water molecules themselves of the water solution 20 are polarized, when the electron beam incident part is charged minus, electric dipoles of the water molecules are arrayed along a potential gradient. According to the electric dipole array, electric charges are also generated on the surface of the second insulative thin film 204 present on the lower side of the water solution 20. The electric charges are detected by the terminal section 210 as a potential signal generated on the principal plane of the second insulative thin film 204 and changes to a measurement signal.

On the other hand, as shown in FIG. 4(b), in the state in which the electron beams 102 is blocked (the OFF state), the incident electrons in the conductive thin film 201 immediately flows into the GND. The minus potential disappears. Consequently, the array of the electric dipoles in the water solution 20 come apart, the electric charges on the surface of the first insulative thin film 203 disappear, and the measurement signal output from the terminal section 210 changes to 0.

By repeating ON/OFF of the electron beam at a frequency of 1 kHz or more, it is possible to extract a signal of a frequency component same as the frequency from the terminal section 210.

Figure 5:
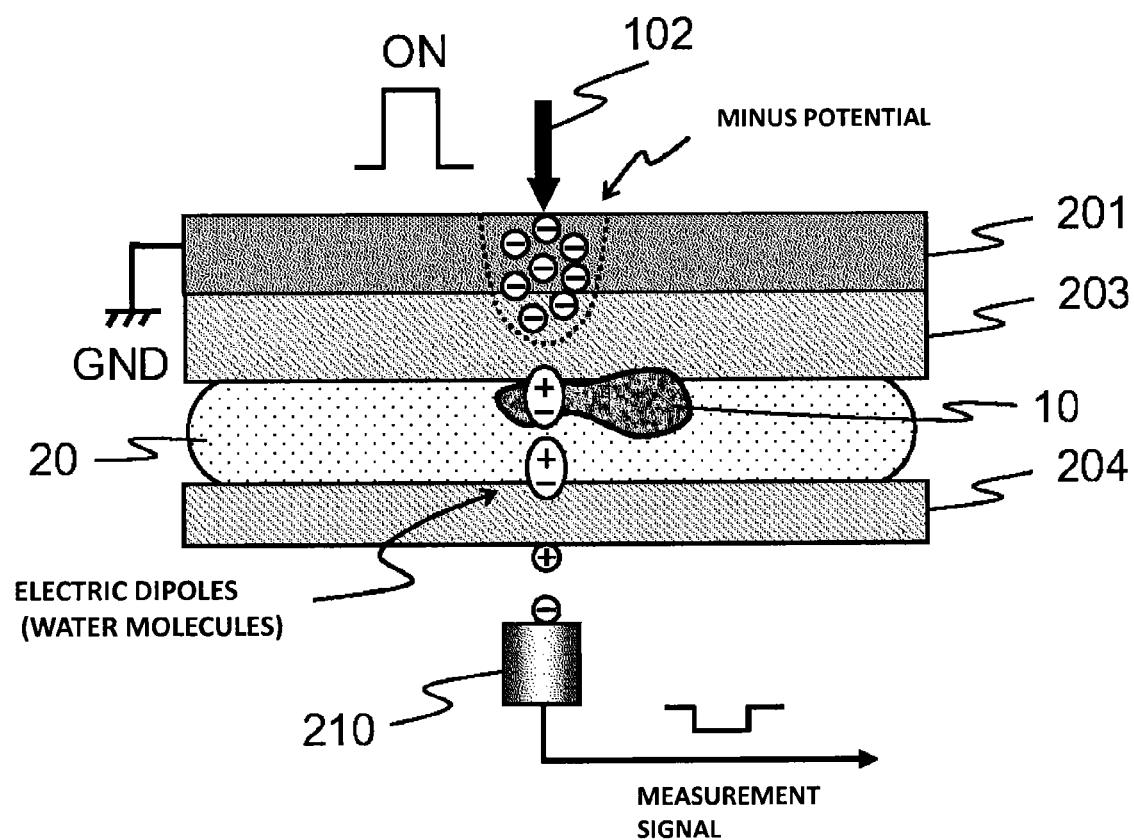
FIG. 5 is a diagram for conceptually explaining a mechanism in which a signal is detected in the terminal section when the electron beam is irradiated on a biological sample, which is an observation sample.

FIG. 5 is a diagram for conceptually explaining a mechanism in which a signal is detected in the terminal section 210 when the electron beam 102 is irradiated on a biological sample, which is the observation sample 10.

When the electron beam 102 is irradiated at a frequency of 1 kHz or more of ON/OFF, since the dielectric constant of the biological sample is extremely low compared with water, the array of the electric dipoles is weakened and the intensity of the measurement signal decreases.

Since the dielectric constant of the water molecules is as large as approximately 80, if a potential change occurs on the one principal plane of the first insulative thin film 203, the potential change can be used as a signal with a strong propagating force in the water solution 20. On the other hand, in general, the dielectric constant of the biological sample 10 is low. For example, the dielectric constant of protein is 2 to 3. Therefore, the propagation force of the potential change signal in the biological sample is weak. Therefore, it is possible to obtain high contrast according to such a large difference in the dielectric constants (the difference in the propagating forces).

As a result, in the biological sample 10 and the water solution 20, a difference occurs in the propagation force of the potential change signal due to the difference in the dielectric constants. The difference is detected by the terminal section 210 provided on the one principal plane side of the first insulative thin film 203. Consequently, it is possible to observe the biological sample at high contrast without dying the biological sample. Moreover, since the electron beam is not directly irradiated on the biological sample 10, the observation sample 10 is not damaged by the electron beam irradiation.

Note that the resolution of an image obtained by observation generally depends on the irradiation diameter of the electron beam. Therefore, if the irradiation diameter of the electron beam is narrowed to approximately 1 nm, it is also possible to attain resolute (1 nm) substantially equal to the irradiation diameter. As a result, a biological sample including bacteria, viruses, protein, or a protein complex can also be observed in a living state at high resolution and high contrast.

EXAMPLES

An example in which bacteria and yeast, which were observation samples, were dissolved in a water solution and encapsulated in the sample holder 200 and scanning electron microscope observation was performed is explained.

Figure 6:
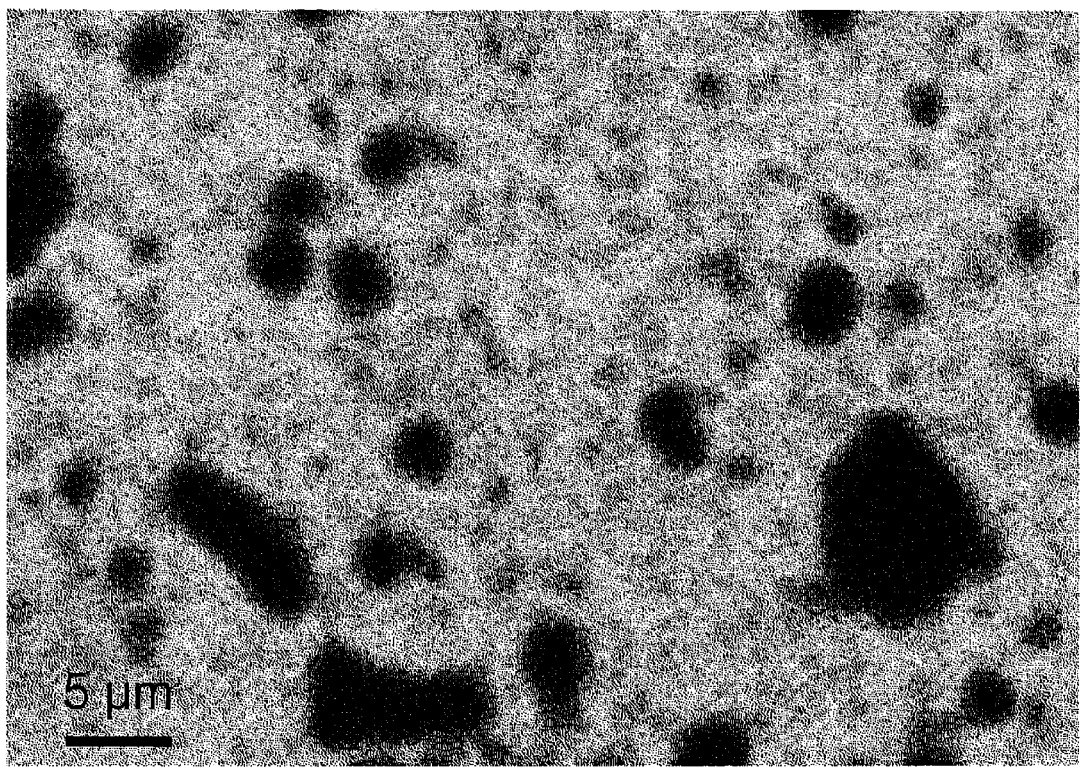
FIG. 6 is an observation image obtained by storing bacteria dissolved in a water solution in the sample holder for the scanning electron microscope according to the present invention and observing the bacteria.

FIG. 6 is an observation image obtained by storing bacteria 10 dissolved in the water solution 20 in the sample holder 200 for the scanning electron microscope according to the present invention and observing the bacteria. The acceleration voltage of the electron beam during the observation is 3 kV and an ON/OFF frequency of the incident electron beam is 30 kHz.

The first insulative thin film 203, which is a sample supporting film, is a silicon nitride film having thickness of 50 nm. The conductive thin film 201 obtained by forming thin films of nickel having thickness of 5 nm and tungsten having thickness of 20 nm is stacked on the first insulative thin film 203 as shown in FIG. 3.

The water solution sample was sandwiched between the first insulative thin film 203 and the second insulative thin film 204 having thickness of 50 nm. The terminal section 210 was set below the second insulative thin film 204 with an air gap provided therebetween.

From this observation image, elongated bacteria of approximately 5 nm and spherical bacteria can be observed. In the observation, although dying treatment and fixation treatment are not applied at all, an image with extremely high contrast is obtained.

FIG. 7 is an observation image obtained by storing yeast 10 dissolved in the water solution 20 in the sample holder 200 for the scanning electron microscope according to the present invention and observing the yeast 10. FIG. 7(a) is an observation image in the case in which an ON/OFF frequency of an incident electron beam is 30 kHz and FIG. 7(b) is an observation image in the case in which the ON/OFF frequency of the incident electron beam is 80 kHz. Note that the acceleration voltage of the electron beam during the observation is 3 kV.

Even when the ON/OFF frequency of the incident electron beam is 30 kHz, yeast having a size around 10 μm can be observed at extremely high contrast. However, when the ON/OFF frequency of the incident electron beam is set to 80 kHz, the observation image is clearer.

Figure 8:
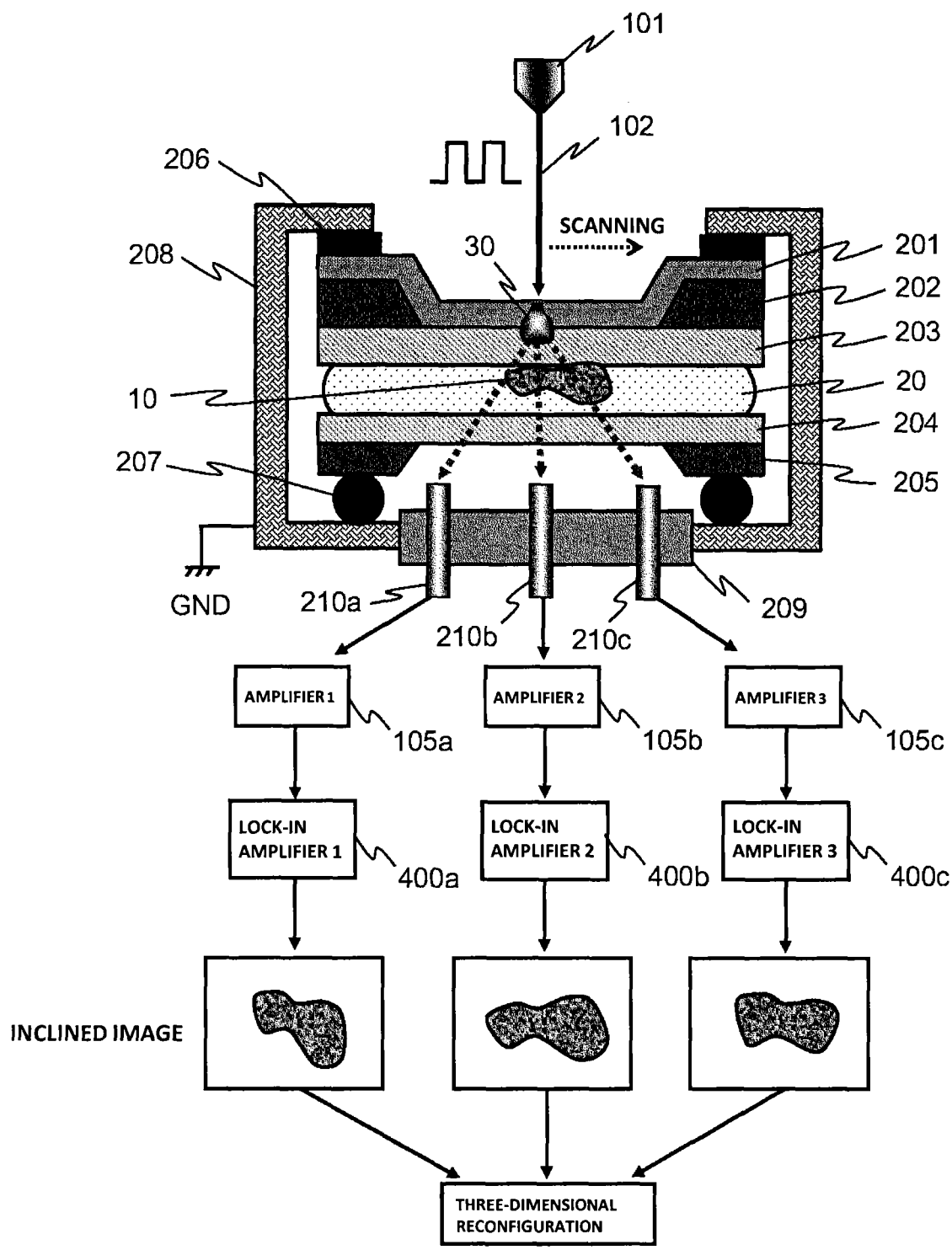
FIG. 8 is a configuration example of a scanning electron microscope image observation system having a form in which a plurality of terminal sections are provided in different positions.

FIG. 8 is a configuration example of a scanning electron microscope image observation system having a form in which a plurality of terminal sections 210a to 210c are provided in different positions. A plurality of amplifiers 105a to 105c and a plurality of lock-in amplifiers 400a to 400c are also provided because the plurality of terminal sections 210a to 210c are provided.

The arithmetic unit forms an image for each of signal components having the intensity change frequency respectively extracted from the plurality of terminal sections, calculates an inclination angle of the image from a relation between an incident position of the electron beam and the positions where the terminal sections are provided, applies correction to the image (an inclined image) on the basis of the inclination angle, and analyzes three-dimensional structure information of an observation sample on the basis of a plurality of images after the correction.

For example, when three terminal sections are provided, an inclined image from the terminal section 210a provided on the left side, an inclined image from the terminal section 210c provided on the right side, and an inclined image from the terminal section 210b at the center present in a position where the observation sample is observed from the front can be obtained in one observation. These three images are constructed as a three-dimensional image using a three-dimensional reconfiguration algorithm according to inclination angles of the images.

FIG. 9 is a diagram for explaining the structure of the sample holder 200 having a form in which a mechanism for adjusting the pressure on the inside of the outer frame section 208 is provided therein. In FIG. 9(a), a state under the atmospheric pressure is shown. In FIG. 9(b), a state in a vacuum (in a microscope chamber) is shown. In an example shown in the figure, a decompression film 211 is formed as a pressure adjusting mechanism and provided on the lower surface side of the outer frame section 208.

The decompression film 211 of the sample holder 200 expands to the outer side in the microscope chamber. The pressure in the holder decreases. The conductive thin film 201 side also bends to the outer side. However, a bending degree is relaxed by the effect of the decompression film 211.

Note that a region below the second insulative thin film 204 is sealed by the O-ring 207 to maintain the atmospheric pressure. Therefore, the second insulative thin film 204 bends upward rather than downward. The gap between the one principal plane of the first insulative thin film 203 and the one principal plane of the second insulative thin film 204 expands. Therefore, no problem occurs in holding the observation sample 10.

In the sample holder 200, a channel for perfusing the water solution may be provided in the gap of the predetermined interval between the one principal plane of the first insulative thin film 203 and the one principal plane of the second insulative thin film 204. A plurality of kinds of solutions may be encapsulated in the sample holder 200 and observed while changing the solutions.

FIG. 10 is a configuration example of a part of the sample holder 200 in which channels for perfusing the water solution are provided in the gap of the predetermined interval between the one principal plane of the second insulative thin film 204 and the one principal plane of the first insulative thin film 203. FIGS. 10(a) to 10(c) are respectively a perspective view, a top view, and a sectional view.

In the example shown in the figure, three channels for perfusing the water solution are provided. The outer frame section 208 of the sample holder 200 includes an upper portion 208a and a lower portion 208b. In the upper portion 208a, injection holes 213 associated with three channels 212 are formed. A solution introduced into these channels 212 is introduced into the gap of the predetermined interval between the one principal plane of the second insulative thin film 204 and the one principal plane of the first insulative thin film 203 by action of surface tension.

Dampers 214 functioning as pressure applying sections for pushing out the solution from the injection holes 213 are provided on a side of the sample holder 200. Pressure applying valves 215 are provided at the distal ends of the dampers 214.

When such a plurality of channels 212 are provided, it is easy to conduct, for example, an experiment for, for example, feeding a reagent or the like anew into the sample holder 200, in which the observation sample 10 such as cells or bacteria are stored in advance, and observing reaction by the reagent in detail. Note that a unit denoted by reference numeral 216 in the figure is a discharge liquid tank. Such feeding of the solution may be performed electrophoretically rather than being performed by the pressure applying section.

INDUSTRIAL APPLICABILITY

As explained above, according to the present invention, it is possible to easily observe a biological sample in a water solution at extremely high contrast without applying dying treatment and fixation treatment to the biological sample. In addition, since damage to the sample due to an electron beam does not occur, it is possible to learn original forms and structures concerning biological samples such as cells, bacteria, viruses, and protein complexes and organic materials susceptible to damage.

REFERENCE SIGNS LIST

10 Observation sample
20 Water solution
30 Diffusion region
100 Scanning electron microscope
200 Sample holder
300 Function generator
400 Lock-in amplifier
500 Data recorder
600 PC
101 Electron gun
102 Electron beam
103 Beam blanking device
104 Diaphragm
105 Amplifier
201 Conductive thin film
202, 205 Frame sections
203 First insulative thin film
204 Second insulative thin film
206 Conductive gasket
207 O-ring
208 Outer frame section
209 Insulating member
210 Terminal section
211 Decompression film
212 Channels
213 Injection holes
214 Dampers
215 Pressure applying valves
216 Discharge liquid tank

The invention claimed is:

1. An observation system for imaging an organic material sample in a water solution, wherein:
the organic material sample is interposed between opposing surfaces of a pair of opposing first and second insulative thin films together with the water solution; an electron beam is scan-irradiated to a conductive thin film provided on the outwardly facing surface of the first insulative thin film while the intensity of the electron beam is changed in an on-off pulsed manner; and a potential change on the outwardly facing surface of the second insulative thin film, the potential change corresponding to a difference between the dielectric constant of the organic material sample and the dielectric constant of the water solution, is detected.

2. The observation system according to claim 1, wherein the electron beam is supplied to the conductive thin film having ground potential from an electron beam gun provided in a scanning electron microscope.

3. The observation system according to claim 1, wherein signal components of intensity change frequencies are extracted from potential signals, and an image of the potential changes is formed on the basis of the signal components.

4. The observation system according to claim 3, wherein the electron beam is supplied to the conductive thin film having ground potential from an electron beam gun provided in a scanning electron microscope.

5. The observation system according to claim 3, wherein a plurality of terminal sections for detecting the potential changes are provided at different positions along the second insulative thin film; an image is formed for each set of the signal components of the intensity change frequencies extracted from each of the terminal sections; an inclination angle of the image is obtained from a positional relation between an incident position of the electron beam and the terminal section; and three-dimensional structure information is obtained by correcting the image on the basis of the inclination angle.

6. The observation system according to claim 5, wherein the electron beam is supplied to the conductive thin film having ground potential from an electron beam gun provided in a scanning electron microscope.

7. The observation system according to claim 5, wherein the extraction of the signal components of the intensity change frequencies is carried out by using one of the methods of a band pass filter method, a lock-in amplifier method, an autocorrelation analysis method, and a Fourier transform analysis method.

8. The observation system according to claim 7, wherein the electron beam is supplied to the conductive thin film having ground potential from an electron beam gun provided in a scanning electron microscope.

9. The observation system according to claim 1, wherein the water solution is perfused between the opposing surfaces of the first and second insulative thin films.

10. The observation system according to claim 9, wherein the electron beam is supplied to the conductive thin film having ground potential from an electron beam gun provided in a scanning electron microscope.

\* \* \* \* \*